(12) United States Patent
Kyle

(10) Patent No.: US 8,426,594 B2
(45) Date of Patent: Apr. 23, 2013

(54) BENZOMORPHAN COMPOUNDS

(75) Inventor: Donald J. Kyle, Yardley, PA (US)

(73) Assignee: Purdue Pharma L.P., Stamford, CT (US)

( * ) Notice: Subject to any disclaimer, the term of this patent is extended or adjusted under 35 U.S.C. 154(b) by 207 days.

(21) Appl. No.: 12/745,472

(22) PCT Filed: Nov. 28, 2008

(86) PCT No.: PCT/IB2008/003311
§ 371 (c)(1),
(2), (4) Date: Aug. 31, 2010

(87) PCT Pub. No.: WO2009/068989
PCT Pub. Date: Jun. 4, 2009

(65) Prior Publication Data
US 2010/0324080 A1 Dec. 23, 2010

Related U.S. Application Data

(60) Provisional application No. 60/991,369, filed on Nov. 30, 2007, provisional application No. 61/077,616, filed on Jul. 2, 2008.

(51) Int. Cl.
*C07D 221/26* (2006.01)

(52) U.S. Cl.
USPC .......................................................... 546/97

(58) Field of Classification Search .................. None
See application file for complete search history.

(56) References Cited

U.S. PATENT DOCUMENTS 3,131,190 A * 4/1964 Zirkle ........................... 546/104
2001/0036951 A1 11/2001 Farrar et al.

FOREIGN PATENT DOCUMENTS
WO WO2009023567 2/2009

OTHER PUBLICATIONS

May et al., Structures related to morphine. VIII. Further syntheses in the benzomorphan series, 22 J.O.C. 1366-9 (1957).*
Ager et al., Structures related to morphine. XIX. Benzomorphans from 3,4-diethylpyridine, 27 J.O.C. 245-7 (1962).*
Saito et al., Structures related to morphine. XX. Stevens reaction in the synthesis of 5-ethyl-2'-hydroxy-2-methyl-(or phen-ethyl)-6,7-benzomorphan, 27 J.O.C. 948-5 (1962).*
Fullerton et al., Structures related to morphine. XXIII. Stereochemistry of 5,9-dialkyl-6,7-benzomorphans, 27 J.O.C. 2144-7 (1962).*
Inubushi et al,. Structure of dendrine, 31 Tetrahedron Letts. 2723-8 (1965).*
Kametani et al., Synthesis of heterocyclic compounds. CDLXXVIII. Syntheses of analgesics. XXX. Conformational studies of diastereoisomeric quaternary ammonium salts of 1,2,3,4,5,6-hexahydro-2,6-methano-3-benzazocines, 9(5) J. Heterocyclic Chem. 1057-9 (1972).*
Vippagunta et al., Crystalline solids, 48 Adv. Drug Delivery Rev. 3-26 (2001).*
Rautio et al., Prodrugs: Design and Clinical Applications, 7 Nat. Rev. Drug Dis., 255-70 (2008).*
Fry "Stereospecific tautomerism in a 1,2-dihydropyridine. A β-benzomorphan synthesis", Journal of Organic Chemistry, vol. 28, 1963, pp. 1869-1874.
Sawa, et al. "Elimination of the 4-hydroxyl group of the alkaloids related to morphine-VII" Tetrahedron, vol. 21, 1965, pp. 1129-1132.
Chignell, et al. "Structures related to morphine. XXVIII. Alternative synthesis of α- and β-2,9-dimethyl-2'-hydroxy-5-propyl-6,7-benzomorphan", Journal of Medicinal Chemistry, vol. 8, 1965, pp. 235-238.
Ager, et al. "Structures related to morphine. XXV. 5-propyl- and 5,9-dipropyl-6,7-benzomorphans and a pharmacologic summary", Journal of Medicinal Chemistry, vol. 6, 1963, pp. 332-335.
Fullerton, et al. "Structures related to morphine. XXIV. Further application of the Stevens rearrangement in the synthesis of diastereoisomeric 6,7-benzomorphans from 3-ethyl-4-methyl- and 4-ethyl-3methylpyridines", Journal of Organic Chemistry, vol. 27, 1962, pp. 2554-2557.
May, et al. "Structures related to morphine. XI. Analogs and a diastereoisomer of 2'-hydroxy-2,5,9-trimethyl-6,7-benzomorphan", Journal of Organic Chemistry, vol. 24, 1959, pp. 1432-1435.

* cited by examiner

*Primary Examiner* — Janet Andres
*Assistant Examiner* — Timothy R Rozof
(74) *Attorney, Agent, or Firm* — Purdue Pharma L.P.; Marian E. Fundytus; Alan L. Koller

(57) ABSTRACT

The invention relates to Benzomorphan Compounds of Formula (I): wherein X, $R^1$, $R^2$, $R^3$, $R^4$, and $R^5$ are as defined herein. These compounds are useful for treating constipation preferably constipation caused by mu-opioid agonist therapy.

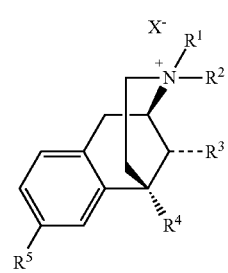

I

14 Claims, No Drawings

BENZOMORPHAN COMPOUNDS

This is the National Stage of PCT application number PCT/IB2008/003311, filed 28 Nov. 2008, which claims the benefit of U.S. provisional application Ser. No. 60/991,369, filed 30 Nov. 2007, and U.S. provisional application Ser. No. 61/077,616, filed 2 Jul. 2008.

FIELD OF THE INVENTION

This invention is in the field of medicinal chemistry. It relates to novel benzomorphan compounds having dual activity as mu opioid antagonists and kappa opioid agonists, which compounds can help reduce or eliminate the problem of constipation in opioid-treated patients.

BACKGROUND OF THE INVENTION

Pain is the most common symptom for which patients seek medical advice and treatment. While acute pain is usually self-limited, chronic pain can persist for 3 months or longer and lead to significant changes in a patient's personality, lifestyle, functional ability and overall quality of life (K. M. Foley, Pain, in Cecil Textbook of Medicine 100-107, J. C. Bennett and F. Plum eds., 20th ed. 1996).

Pain has traditionally been managed by administering either a non-opioid analgesic (such as acetylsalicyclic acid, choline magnesium trisalicylate, acetaminophen, ibuprofen, fenoprofen, diflunisal or naproxen), or an opioid analgesic (such as morphine, hydromorphone, methadone, levorphanol, fentanyl, oxycodone or oxymorphone).

Use of opioid analgesics often leads to constipation as a side effect. Constipation associated with the use of opioid analgesics is presumed to occur primarily and mechanistically as a result of the action of mu opioid agonists directly upon mu opioid receptors located in the bowel (Wood & Galligan (2004), Function of opioids in the enteric nervous system. *Neurogastroenterology & Motility* 16(Suppl.2): 17-28.). Stimulation of the mu opioid receptors in the bowel causes inhibition of normal gastrointestinal (GI) motility, leading to constipation. The effect of mu opioid agonism on mu opioid receptors in the bowel can be observed via the action of loperamide (Imodium™) in treating diarrhea. Loperamide is a potent mu opioid agonist that is administered orally, but which has little to no absorption into the blood stream. As a result, loperamide exerts its action locally upon the mu opioid receptors in the bowel, and this results in inhibition of GI motility, which treats diarrhea.

There has been recent interest in developing combinations of mu receptor agonists and antagonists having defined biodistribution properties that might serve to limit opioid-induced constipation. For example, the co-administration of an orally bio-available mu opioid receptor agonist (such as morphine, codeine, oxycodone or hydromorphone) together with a potent mu opioid receptor antagonist (such as N-methylnaloxone or N-methylnaltrexone) that is not orally bio-available may serve to prevent or reduce the constipation otherwise associated with mu opioid receptor agonist therapy. The rationale is that the agonist component will be absorbed and distributed throughout the periphery and the central nervous system (CNS), resulting in the desired analgesia, while the antagonist component will remain in the bowel where it will prevent or reduce any agonist-induced constipation that might otherwise occur.

BRIEF SUMMARY OF THE INVENTION

The present invention is related to novel benzomorphan compounds useful for treating or preventing constipation, preferably mu opioid receptor-induced constipation. More specifically, the present invention provides compounds of Formula I below, and the pharmaceutically acceptable salts, prodrugs and solvates thereof having activity as mu receptor antagonists (collectively referred to hereafter as "Compounds of the Invention"; individually referred to hereafter as "Compound of the Invention"). In certain embodiments, Compounds of the Invention are expected to have dual activity as both mu receptor antagonists and kappa receptor agonists. Certain Compounds of the Invention are expected to be substantially restricted to the GI tract.

Compounds of the Invention that have mu antagonist activity and are substantially restricted to the GI tract will significantly reduce or prevent constipation that would otherwise occur in a patient as a result of treatment with a mu agonist. In one embodiment, the reduction or prevention of constipation is obtained without reducing the desired analgesic effect of the mu agonist. Compounds of the Invention that also exhibit kappa agonist activity should additionally stimulate GI motility via a non-mu receptor mediated mechanism.

The present invention further provides pharmaceutical compositions useful for treating or preventing constipation, preferably constipation caused by mu-opioid agonist therapy, said pharmaceutical composition comprising an effective amount of a Compound of the Invention admixed with one or more pharmaceutically acceptable carriers or excipients. In one embodiment, the pharmaceutical composition comprises an effective amount of a Compound of the Invention, an analgesically effective amount of a mu agonist, and one or more pharmaceutically acceptable carriers or excipients.

The present invention further provides a method for treating or preventing constipation, preferably constipation associated with mu-opioid agonist therapy, by administering an effective amount of a Compound of the Invention to a patient in need of such treatment or prevention. In one embodiment, the Compound of the Invention is a mu antagonist that is substantially restricted to the GI tract. In another embodiment, the Compound of the Invention is both a mu antagonist and a kappa agonist, and is substantially restricted to the GI tract. In another embodiment, the method comprises co-administering to a patient both an effective amount of a Compound of the Invention that is a mu antagonist and is substantially restricted to the GI tract, and an analgesically effective amount of a mu agonist. In another embodiment, the method comprises co-administration to a patient of both an effective amount of a Compound of the Invention that is both a mu antagonist and a kappa agonist, and which is substantially restricted to the GI tract, and an analgesically effective amount of a mu agonist.

The present invention further provides a method of modulating activity of at least one type of opioid receptor comprising exposing the receptor to an effective amount of a Compound of the Invention. In one embodiment, the opioid receptor is located in the GI tract. In another embodiment, the receptor is a mu receptor. In another embodiment, the receptor is a kappa receptor. In another embodiment, the Compound of the Invention modulates both a mu receptor and a kappa receptor in the GI tract. In another embodiment, the Compound of the Invention antagonizes the mu receptor. In another embodiment, the Compound of the Invention agonizes the kappa receptor. In another embodiment the Compound of the Invention both antagonizes the mu receptor and agonizes the kappa receptor.

The Compound of the Invention can be radiolabeled and used as a radioligand for binding to an opioid receptor. Utilizing such radiolabeled compounds (e.g. radiolabeled with $^3$H, $^{11}$C or $^{14}$C), the present invention further provides methods for screening a candidate compound for the ability to bind to an opioid receptor. In one embodiment, such a method comprises: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

In a further aspect, the present invention provides the use of a Compound of the Invention in the manufacture of a medicament for treating or preventing constipation preferably constipation associated with mu receptor agonist therapy, in a mammal.

DETAILED DESCRIPTION OF THE INVENTION

The Compounds of the Invention are quaternized benzomorphan compounds of Formula I as defined below, and include the pharmaceutically acceptable salts, prodrugs and solvates thereof, which are useful as opioid receptor modulators. Compounds of the Invention are expected to selectively antagonize mu (μ) opioid receptors. In addition, certain Compounds of the Invention are expected to also activate kappa (κ) opioid receptors. Compounds of the Invention are useful for treating or preventing constipation, preferably constipation associated with mu agonist therapy.

The present invention encompasses compounds according to Formula I,

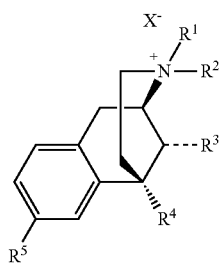

wherein
$R^1$ and $R^2$ are each independently selected from the group consisting of —($C_1$-$C_{10}$)alkyl, —($C_2$-$C_{10}$)alkenyl, —($C_2$-$C_{10}$)alkynyl, —($C_3$-$C_{12}$)cycloalkyl, —($C_3$-$C_{12}$)cycloalkenyl, —($CH_2$)$_n$—O—($CH_2$)$_n$—$CH_3$, ($C_1$-$C_{10}$)alkoxy, C(halo)$_3$, CH(halo)$_2$, CH$_2$(halo), C(O)$R^6$, —C(O)O—($C_1$-$C_{10}$)alkyl, and —($CH_2$)$_n$—N($R^7$)$_2$, each of which is optionally substituted by 1, 2, or 3 independently selected $R^8$ groups;
$R^3$ and $R^4$ are each independently selected from
(a) —H; or
(b) —($C_1$-$C_5$)alkyl, —($C_2$-$C_5$)alkenyl, and —($C_2$-$C_5$)alkynyl;
$R^5$ is selected from
(a) —H, —OH, halo, —C(halo)$_3$, —CH(halo)$_2$, and —CH$_2$(halo)
(b) —($C_1$-$C_5$)alkyl, —($C_2$-$C_5$)alkenyl, —($C_2$-$C_5$)alkynyl, —($CH_2$)$_n$—O—($CH_2$)$_n$—$CH_3$, —($C_1$-$C_5$)alkoxy, each of which is optionally substituted with 1, 2, or 3 independently selected $R^8$ groups;
$R^6$ is selected from —H, —($C_1$-$C_{10}$)alkyl, —($C_2$-$C_{10}$)alkenyl, —($C_2$-$C_{10}$)alkynyl, and —($C_1$-$C_{10}$)alkoxy;
each $R^7$ is independently selected from —H, —($C_1$-$C_{10}$)alkyl, —($C_2$-$C_{10}$)alkenyl, and —($C_2$-$C_{10}$)alkynyl;

each $R^8$ is independently selected from —OH, halo, —($C_1$-$C_{10}$)alkyl, —($C_2$-$C_{10}$)alkenyl, —($C_2$-$C_{10}$)alkynyl, —($C_1$-$C_{10}$)alkoxy, —($C_3$-$C_{12}$)cycloalkyl, —CHO, —C(O)OH, —C(halo)$_3$, —CH(halo)$_2$, CH$_2$(halo), and —($CH_2$)$_n$—O—($CH_2$)$_n$—$CH_3$;
$X^-$ is an organic or inorganic anion, such as sulfate; citrate; acetate; dichloroacetate; trifluoroacetate; oxalate; halide, such as chloride, bromide, iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucoronate; saccharate; formate; mandelate; formate; arginate; carboxylate; benzoate; glutamate; methanesulfonate; ethanesulfonate; benzenesulfonate; p-toluenesulfonate; and pamoate (i.e., 1,1'-methylene-bis-(2-hydroxy-3-naphthoate));
each n is independently selected from an integer from 0, 1, 2, 3, 4, 5, or 6 or a solvate or prodrug thereof;
In another embodiment the present invention provides compounds represented by Formula Ia:

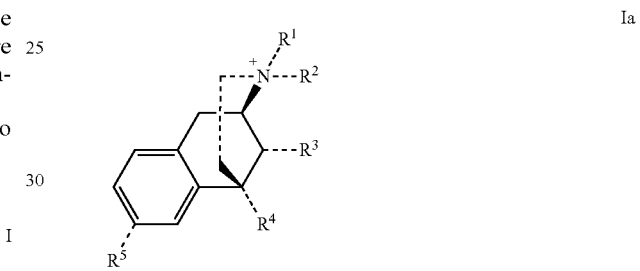

wherein:
$R^1$ and $R^2$ are each independently selected from the group consisting of —($C_1$-$C_{10}$)alkyl, —($C_2$-$C_{10}$)alkenyl, —($C_2$-$C_{10}$)alkynyl, —($C_3$-$C_{12}$)cycloalkyl, —($C_3$-$C_{12}$)cycloalkenyl, —($CH_2$)$_n$—O—($CH_2$)$_n$—$CH_3$, —($C_1$-$C_{10}$)alkoxy, —C(halo)$_3$, —CH(halo)$_2$, —CH$_2$(halo), —C(O)$R^6$, —C(O)O—($C_1$-$C_{10}$)alkyl, and —($CH_2$)$_n$—N($R^7$)$_2$, each of which is optionally substituted by 1 to 3 $R^8$ groups;
$R^3$ and $R^4$ are each independently selected from H, —($C_1$-$C_5$)alkyl, —($C_2$-$C_5$)alkenyl, and —($C_2$-$C_5$)alkynyl;
$R^5$ is selected from H, OH, halo, —($C_1$-$C_5$)alkyl, —($C_2$-$C_5$)alkenyl, —($C_2$-$C_5$)alkynyl, —($CH_2$)$_n$—O—($CH_2$)$_n$—$CH_3$, —($C_1$-$C_5$)alkoxy, —C(halo)$_3$, —CH(halo)$_2$, and —CH$_2$(halo);
$R^6$ is selected from H, —($C_1$-$C_{10}$)alkyl, —($C_2$-$C_{10}$)alkenyl, —($C_2$-$C_{10}$)alkynyl, and —($C_1$-$C_{10}$)alkoxy;
each $R^7$ is independently selected from H, —($C_2$-$C_{10}$)alkenyl, and —($C_2$-$C_{10}$)alkynyl;
each $R^8$ is independently selected from OH, halo, —($C_1$-$C_{10}$)alkyl, —($C_2$-$C_{10}$)alkenyl, —($C_2$-$C_{10}$)alkynyl, $C_{1-10}$alkoxy, —($C_3$-$C_{12}$)cycloalkyl, —C(=O)OH, —C(halo)$_3$, —CH(halo)$_2$, —CH$_2$(halo), and —($CH_2$)$_n$—O—($CH_2$)$_n$—$CH_3$;
each n is an independently selected integer from 0 to 6;
and pharmaceutically acceptable salts, solvates and prodrugs thereof.

In one embodiment, at least one of $R^1$ and $R^2$ is a ($C_1$-$C_{10}$) alkyl substituted with at least one $R^8$ group. In a preferred embodiment $R^8$ is selected as —($C_3$-$C_{12}$)cycloalkyl. In a more preferred embodiments, $R^8$ is selected from cyclopropyl, cyclopentyl, cyclohexyl, cycloheptyl, cyclooctyl, cyclononyl and cyclodecyl.

In another embodiment, at least one of $R^1$ and $R^2$ is a —$(C_2$-$C_{10})$alkenyl. In a more specific embodiment, at least one of $R^1$ and $R^2$ is a —$(C_2$-$C_5)$alkenyl. In another embodiment at least one of $R^1$ and $R^2$ is —$CH_2$-cyclopropyl, —$CH_2CH_2$-cyclopropyl, and $CH_2CH_2CH_2$-cyclopropyl. In a preferred embodiment at least one of $R^1$ or $R^2$ is $CH_2$-cyclopropyl.

In another embodiment, $R^3$ and $R^4$ are each independently selected from a —$(C_1$-$C_5)$alkyl. In a more specific embodiment, each of $R^3$ and $R^4$ is independently selected from methyl, ethyl, and propyl.

In another embodiment, $R^5$ is —OH.

In another embodiment, $R^5$ is —$(CH_2)_n$—O—$(CH_2)_n$—$CH_3$. In a more specific embodiment, $R^5$ is selected from —$(CH_2)$—O—$CH_3$ and —$(CH_2)$—O—$(CH_2)$—$CH_3$.

In one embodiment wherein $R^1$, $R^3$ and $R^4$ are each —$CH_3$ and $R^5$ is —OH, $R^2$ is not —$CH_2$—CH=$C(CH_3)_2$.
In another embodiment wherein $R^2$, $R^3$ and $R^4$ are each —$CH_3$ and $R^5$ is —OH, $R^1$ is not —$CH_2$—CH=$C(CH_3)_2$.
In another embodiment wherein $R^1$ is selected from —$CH_3$ or —$CD_3$, $R^3$ and $R^4$ are each selected as —$CH_3$, and $R^5$ is —OH, $R^2$ is not —$CH_3$ or —$CD_3$;
In another embodiment wherein $R^1$ is selected as —$CH_3$ or —$C_2H_5$, $R^3$ and $R^4$ are each selected as —$CH_3$, and $R^5$ is —OH, $R^2$ is not —$CH_3$ or —$C_2H_5$; and
In another embodiment wherein $R^1$, $R^2$, $R^3$, and $R^4$ are each selected as —$CH_3$, then $R^5$ is not -halo.
In another embodiment, each n is independently selected from 1, 2 and 3.

Specific compounds of the present invention include:
3-cyclopropylmethyl-9-hydroxy-3,6,11-trimethyl-1,2,3,4,5,6-hexahydro-2,6-methano-benzo[d]azocinium; and
3-allyl-9-hydroxy-3,6,11-trimethyl-1,2,3,4,5,6-hexahydro-2,6-methano-benzo[d]azocinium;
and the pharmaceutically acceptable salts, solvates and prodrugs thereof.

As used herein, the term "$(C_1$-$C_{10})$alkyl" refers to a straight-chain and branched non-cyclic saturated hydrocarbon having from 1 to 10 carbon atoms. Representative straight chain —$(C_1$-$C_{10})$alkyl groups include methyl, -ethyl, -n-propyl, -n-butyl, -n-pentyl, -n-hexyl, n-heptyl, n-octyl, n-nonyl and n-decyl. Representative branched —$(C_1$-$C_{10})$ alkyl groups include isopropyl, sec-butyl, isobutyl, tert-butyl, isopentyl, neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethtylbutyl, 1,2-dimethylbutyl, 1,3-dimethylbutyl, 2,2-dimethylbutyl, 2,3-dimethylbutyl, and 3,3-dimethylbutyl.

As used herein, the term "$(C_1$-$C_5)$alkyl" refers to a straight-chain and branched non-cyclic saturated hydrocarbon having from 1 to 5 carbon atoms. Representative straight chain —$(C_1$-$C_5)$alkyl groups include methyl, -ethyl, -n-propyl, -n-butyl, and -n-pentyl. Representative branched-chain —$(C_1$-$C_5)$alkyl groups include isopropyl, sec-butyl, isobutyl, tert-butyl, isopentyl, neopentyl, 1-methylbutyl, 2-methylbutyl, 3-methylbutyl, 1,1-dimethylpropyl, and 1,2-dimethylpropyl.

As used herein, the term "$(C_2$-$C_{10})$ alkenyl" refers to a straight chain and branched non-cyclic hydrocarbon having from 2 to 10 carbon atoms and including at least one carbon-carbon double bond. Representative straight chain and branched —$(C_2$-$C_{10})$ alkenyl groups include -vinyl, allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, -1-hexenyl, -2-hexenyl, and 3-hexenyl.

As used herein, the term "$(C_2$-$C_5)$alkenyl" refers to straight chain and branched non-cyclic hydrocarbons having from 2 to 5 carbon atoms and including at least one carbon-carbon double bond. Representative straight chain and branched —$(C_2$-$C_5)$alkenyl groups include -vinyl, allyl, -1-butenyl, -2-butenyl, -isobutylenyl, -1-pentenyl, -2-pentenyl, -3-methyl-1-butenyl, and -2-methyl-2-butenyl.

As used herein, the term "$(C_2$-$C_{10})$alkynyl" refers to straight chain and branched non-cyclic hydrocarbons having from 2 to 10 carbon atoms and including at least one carbon-carbon triple bond. Representative straight chain and branched $C_2$-$C_{10}$ alkynyl groups include -acetylenyl, -propynyl, -1 butynyl, -2-butynyl, -1-pentynyl, -2-pentynyl, -3-methyl-1-butynyl, -4-pentynyl, -1-hexynyl, -2-hexynyl, and -5-hexynyl.

As used herein, the term "—$(C_2$-$C_5)$alkynyl" refers to straight chain and branched non-cyclic hydrocarbons having from 2 to 5 carbon atoms and including at least one carbon-carbon triple bond. Representative straight chain and branched —$(C_2$-$C_5)$alkynyl groups include -acetylenyl, -propynyl, -1 butynyl, -2-butynyl, -1-pentynyl, -2-pentynyl, -3-methyl-1-butynyl, and -4-pentynyl.

As used herein, the term "$(C_3$-$C_{12})$cycloalkyl" refers to a cyclic saturated hydrocarbon having from 3 to 12 carbon atoms, and selected from cyclopropyl, cyclobutyl, cyclopentyl, cyclohexyl, cycloheptyl, cyclooctyl, and cyclononyl, cyclodecyl, cycloundecyl and cyclododecyl.

As used herein, the term "$(C_3$-$C_{12})$cycloalkenyl" refers to a cyclic hydrocarbon having from 3 to 12 carbon atoms, and including at least one carbon-carbon double bond, including cyclopropenyl, cyclobutenyl, cyclopentenyl, cyclohexenyl, cycloheptenyl, cyclooctenyl, and cyclononenyl, cyclodecenyl, cycloundecenyl and cyclododecenyl.

As used herein, the terms "halo" and "halogen" refer to fluoro, chloro, bromo or iodo.

"—$(C_1$-$C_{10})$alkoxy" means a straight chain or branched non-cyclic hydrocarbon having one or more ether groups and from 1 to 10 carbon atoms. Representative straight chain and branched $(C_1$-$C_{10})$alkoxys include -methoxy, -ethoxy, propoxy, butyloxy, pentyloxy, hexyloxy, heptyloxy, methoxymethyl, 2-methoxyethyl, -5-methoxypentyl, 3-ethoxybutyl and the like.

"—$(C_1$-$C_5)$alkoxy" means a straight chain or branched non-cyclic hydrocarbon having one or more ether groups and from 1 to 5 carbon atoms. Representative straight chain and branched $(C_1$-$C_5)$alkoxys include -methoxy, -ethoxy, propoxy, butyloxy, pentyloxy, methoxymethyl, 2-methoxyethyl, -5-methoxypentyl, 3-ethoxybutyl and the like.

"—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

"—$CH(halo)_2$" means a methyl group where two of the hydrogens of the methyl group have been replaced with a halogen. Representative —$CH(halo)_2$ groups include —$CHF_2$, —$CHCl_2$, —$CHBr_2$, —$CHBrCl$, —$CHClI$, and —$CHI_2$.

"—$C(halo)_3$" means a methyl group where each of the hydrogens of the methyl group has been replaced with a halogen. Representative —$C(halo)_3$ groups include —$CF_3$, —$CCl_3$, —$CBr_3$, and —$CI_3$.

"-Halogen" or "-halo" means —F, —Cl, —Br, or —I.

As used herein, the term "optionally substituted" refers to a group that is either unsubstituted or substituted.

Compounds of the Invention can be in the form of prodrugs of the compounds of Formula I. Prodrugs are covalently bonded carrier molecules that release an active compound of Formula I in vivo. Non-limiting examples of prodrugs typically include esters of the compounds of Formula I that can be metabolized to the active compound by the action of enzymes in the body. Such prodrugs may be prepared by reacting a compound of Formula I with an anhydride such as succinic anhydride.

The present invention further provides isotopically-labeled (i.e., radio-labeled) compounds of Formula I. Examples of isotopes that can be incorporated into the disclosed compounds include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$, respectively, and preferably $^3H$, $^{11}C$, and $^{14}C$. Isotopically-labeled compounds of Formula I can be prepared by methods known in the art in view of this disclosure. For example, tritiated compounds of Formula I can be prepared by introducing tritium into the particular compound of Formula I by catalytic dehalogenation with tritium. This method may include reacting a suitable halogen-substituted precursor of a compound of Formula I with tritium gas in the presence of an appropriate catalyst such as Pd/C in the presence of a base. Other suitable methods for preparing tritiated compounds are generally described in Filer, Isotopes in the Physical and Biomedical Sciences, Vol. 1, Labeled Compounds (Part A), Chapter 6 (1987). $^{14}C$-labeled compounds can be prepared by employing starting materials having a $^{14}C$ carbon.

Isotopically labeled Compounds of the Invention, as well as the pharmaceutically acceptable salts, prodrugs and solvates thereof, can be used as radioligands to test for the binding of compounds to an opioid receptor. For example, a radio-labeled compound of Formula I can be used to characterize specific binding of a test or candidate compound to the receptor. Binding assays utilizing such radio-labeled compounds can provide an alternative to animal testing for the evaluation of chemical structure-activity relationships. In a non-limiting embodiment, the present invention provides a method for screening a candidate compound for the ability to bind to an opioid receptor, comprising the steps of: a) introducing a fixed concentration of the radio-labeled compound to the receptor under conditions that permit binding of the radio-labeled compound to the receptor to form a complex; b) titrating the complex with a candidate compound; and c) determining the binding of the candidate compound to said receptor.

Compounds of the Invention disclosed herein may contain one or more asymmetric centers, thus giving rise to enantiomers, diastereomers, and other stereoisomeric forms. The present invention encompasses all such possible forms, as well as their racemic and resolved forms and mixtures thereof, and the uses thereof. The individual enantiomers may be separated according to methods known to those of ordinary skill in the art in view of the present disclosure. When the compounds described herein contain olefinic double bonds or other centers of geometric asymmetry, and unless specified otherwise, they include both E and Z geometric isomers. All tautomers are intended to be encompassed by the present invention as well.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

The term "chiral center" refers to a carbon atom to which four different groups are attached.

The terms "enantiomer" and "enantiomeric" refer to a molecule that cannot be superimposed on its mirror image and hence is optically active such that the enantiomer rotates the plane of polarized light in one direction and its mirror image compound rotates the plane of polarized light in the opposite direction.

The term "racemic" refers to a mixture of equal parts of enantiomers and which mixture is optically inactive.

The term "resolution" refers to the separation or concentration or depletion of one of the two enantiomeric forms of a molecule.

The terms "a" and "an" refer to one or more.

Suitable anions ($X^-$) for the Compounds according to formula I include inorganic and organic anions such as, but are not limited to, sulfate; citrate; acetate; dichloroacetate; trifluoroacetate; oxalate; halide, such as chloride, bromide, iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucoronate; saccharate; formate; mandelate; formate; arginate; carboxylate; benzoate; glutamate; methanesulfonate; ethanesulfonate; benzenesulfonate; p-toluenesulfonate; and pamoate (i.e., 1,1'-methylene-bis-(2-hydroxy-3-naphthoate)). In case the charge of the anion is greater than required by the cation to yield a neutral compound, the anion is either present in an sub-stoichometric amount (e.g. only 0.5 $SO_4^{2-}$ to neutralize a cation) to result a neutral compound or the remaining charge is neutralized by a further positive charged species such as $H^+$, $K^+$, $Na^+$, $Li^+$, etc (e.g. $HSO_4^{2-}$ to neutralize a cation).

Compounds of the Invention encompass all salts of the disclosed compounds of Formula I. The present invention preferably includes any and all non-toxic, pharmaceutically acceptable salts of the disclosed compounds. Examples of pharmaceutically acceptable salts include inorganic and organic acid addition salts and basic salts. The pharmaceutically acceptable salts include, but are not limited to, metal salts such as sodium salt, potassium salt, cesium salt, and the like; alkaline earth metals such as calcium salt, magnesium salt and the like; organic amine salts such as triethylamine salt, pyridine salt, picoline salt, ethanolamine salt, triethanolamine salt, dicylohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, glutamate and the like.

Acid addition salts can be formed by mixing a solution of the particular compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts can be formed by mixing a solution of the particular compound of the present invention and a pharmaceutically acceptable non-toxic base such as sodium hydroxide, potassium hydroxide, choline hydroxide, sodium carbonate and the like.

Compounds of the Invention also encompass solvates of the disclosed compounds of Formula I. The term "solvate" as used herein is a combination, physical association and/or solvation of a compound of Formula I with a solvent molecule such as, e.g. a disolvate, monosolvate or hemisolvate, where the ratio of solvent molecule to compound of Formula I is 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. A compound of Formula I may be present as a solvated form with a pharmaceutically acceptable solvent, such as water, methanol, ethanol, and the like, and it is intended that the invention include both solvated and unsolvated forms of Formula I compound. One type of solvate is a hydrate. A "hydrate" relates to a particular subgroup of solvates where the solvent molecule is water. Solvates typically can function as pharmacological equivalents. Preparation of solvates is known in the art. See, for example, M. Caira et al, *J. Pharmaceut. Sci.*, 93(3):601-611 (2004), which describes the preparation of solvates of fluconazole with ethyl acetate and with water. Similar preparation of solvates, hemisolvates, hydrates, and the like are described by E. C. van Tonder et al., *AAPS Pharm. Sci. Tech.*, 5(1):Article 12 (2004), and A. L. Bingham et al., *Chem. Commun.*, 603-604 (2001). A typical, non-limiting, process of preparing a solvate would involve dissolving a compound of Formula I in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides the use of a Compound of the Invention in the manufacture of a medicament for treating or preventing constipation, preferably mu receptor agonist-induced constipation. In one embodiment, the Compound of the Invention has activity as a mu receptor antagonist. In another embodiment, the Compound of the Invention has dual activity as both a mu receptor antagonist and a kappa receptor agonist. In another embodiment, the Compound of the Invention is substantially restricted to the GI tract.

Synthesis of Compounds

Compounds of Formula I can be made using conventional organic synthesis in view of this disclosure, or by the illustrative methods shown in the scheme below.

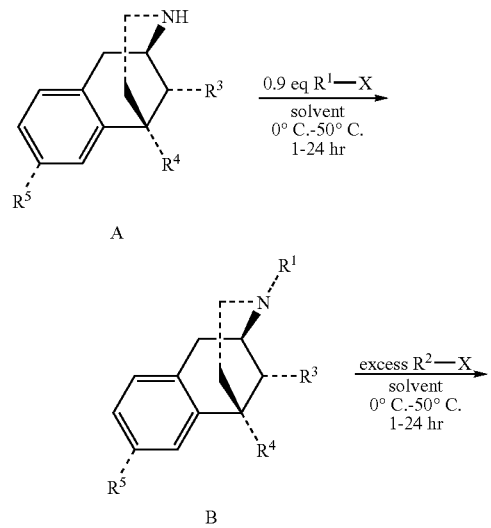

A

B

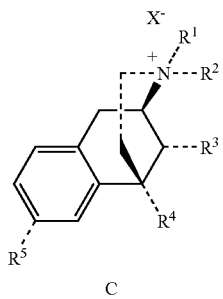

C

Compounds of general structure A are either commercially available, or can be synthesized according to methods known to one skilled in the art (see for example Eddy. and May. *Synthetic Analgesics, Part B*: Pergamon Press: Oxford, London, 1966; Rice and Jacobson (1976). *J. Med Chem.* 19: 430; Lednicer and Mitscher., John Wiley & Sons: New York, 1977, pp 286-312; Palmer and Strauss (1977). *J Chem Rev.* 77: 1; Lednicer. *Central Analgesics*, John Wiley & Sons: New York, 1982, pp 137-213; Brine et al. (1990). *J. Heterocycl. Chem.* 27: 2139; Lednicer. *Strategies for Organic Drug Synthesis and Design*, John Wiley & Sons: New York, 1998, pp 161-184). To obtain a compound of general structure B, a corresponding compound of general structure A (about 0.5-1 mmol) is suspended in 0.5-3 ml dry inert solvent (such as acetonitrile, toluene or xylene) and stirred under nitrogen. About 0.5-1 mmol $R^1$—X (wherein X is a halogen such as Cl, Br or I) is added dropwise with a syringe. The mixture is stirred for about 1 to 24 hr. When the reaction is complete (as monitored by LC/MS and TLC), the solvent is removed. Impurities are removed by flash chromatography using a column of alumina basic as the stationary media, with a gradient of EtOAc in hexane followed by 15% MeOH in DCM as the eluent. Further purification is conducted by chromatography using a column of normal silica with the same two solvent systems as above. The purified material, compound B, is concentrated in vacuo. To obtain compound C, compound B is suspended in 0.5-3 ml dry inert solvent, and an excess of $R^2$—X (about 10-15 equivalents) is added in a single portion. The solution is stirred at ambient temperature for 1-3 hr, and the reaction is followed by LC/MS and TLC. The volatile materials are removed in vacuo, leaving pure compound C.

Testing of Compounds

μ-opioid Receptor Binding Assay Procedures:
Radioligand dose-displacement binding assays for μ-opioid receptors used 0.2 nM[$^3$H]-diprenorphine (NEN, Boston, Mass.), with 5-20 mg membrane protein/well in a final volume of 500 μl binding buffer (10 mM MgCl$_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 1-2 hr at room temperature. Binding reactions were terminated by rapid filtration onto 96-well Unifilter GF/C filter plates (Packard, Meriden, Conn.) presoaked in 0.5% polyethylemimine using a 96-well tissue harvester (Brandel, Gaithersburg, Md.) followed by performing three filtration washes with 500 μl of ice-cold binding buffer. Filter plates were subsequently dried at 50° C. for 2-3 hours. BetaScint scintillation cocktail (Wallac, Turku, Finland) was added (50 μl/well), and plates were counted using a Packard Top-Count for 1 min/well. The data were analyzed using the one-site competition curve fitting functions in GraphPad PRISM v. 3.0 (San Diego, Calif.), or an in-house function for one-site competition curve-fitting.

μ-opioid Receptor Binding Data:

Generally, the lower the Ki value, the more effective the Compounds of the Invention will be at treating pain or diarrhea. Typically, the Compounds of the Invention will have a Ki (nM) of about 300 or less for binding to μ-opioid receptors. In one embodiment, Compounds of the Invention will have a Ki (nM) of about 100 or less. In another embodiment, Compounds of the Invention will have a Ki (nM) of about 10 or less. In still another embodiment, Compounds of the Invention will have a Ki (nM) of about 1 or less. In still another embodiment, Compounds of the Invention will have a Ki (nM) of about 0.1 or less.

μ-Opioid Receptor Functional Assay Procedures:

[$^{35}$S]GTPγS functional assays were conducted using freshly thawed μ-receptor membranes. Assay reactions were prepared by sequentially adding the following reagents to binding buffer (100 mM NaCl, 10 mM MgCl$_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; NEN). The prepared membrane solution (190 μl/well) was transferred to 96-shallow well polypropylene plates containing 10 μl of 20× concentrated stock solutions of the agonist DAMGO prepared in dimethyl sulfoxide (DMSO). Plates were incubated for 30 min at about 25° C. with shaking. Reactions were terminated by rapid filtration onto 96-well Unifilter GF/B filter plates (Packard, Meriden, Conn.) using a 96-well tissue harvester (Brandel, Gaithersburg, Md.), followed by three filtration washes with 200 μl of ice-cold wash buffer (10 mM NaH$_2$PO$_4$, 10 mM Na$_2$HPO$_4$, pH 7.4). Filter plates were subsequently dried at 50° C. for 2-3 hr. BetaScint scintillation cocktail (Wallac, Turku, Finland) was added (50 μl/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data:

μ GTP EC$_{50}$ is the concentration of a compound providing 50% of the maximal response for the compound at a μ-opioid receptor. Compounds of the Invention will typically have a μ GTP EC$_{50}$ (nM) of about 5000 or less to stimulate μ-opioid receptor function. In certain embodiments, Compounds of the Invention will have a μ GTP EC$_{50}$ (nM) of about 2000 or less; or about 1000 or less; or about 100 or less; or about 10 or less; or about 1 or less; or about 0.1 or less.

μ GTP Emax (%) is the maximal effect elicited by a compound relative to the effect elicited by [D-Ala$^2$, N-methyl-Phe$^4$ Gly-ol$^5$]-enkephalin (a/k/a DAMGO), a standard μ agonist. Generally, the μ GTP Emax (%) value measures the efficacy of a compound to treat or prevent pain or diarrhea. Typically, as μ-opioid antagonists, Compounds of the Invention will have a μ GTP Emax (%) of less than about 50%. In certain embodiments, Compounds of the Invention will have a μ GTP Emax (%) of less than about 40%; or less than about 30%; or less than about 20%; or less than about 10%.

κ-opioid Receptor Binding Assay Procedures:

Membranes from recombinant HEK-293 cells expressing the human kappa opioid receptor (kappa) (cloned in house) were prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets were resuspended in hypotonic buffer to a final concentration of 1-3 mg/mL. Protein concentrations were determined using the BioRad protein assay reagent with bovine serum albumen as standard. Aliquots of kappa receptor membranes were stored at −80° C.

Radioligand dose displacement assays used 0.4-0.8 nM [$^3$H]-U69,593 (NEN; 40 Ci/mmole) with 10-20 μg membrane protein (recombinant kappa opioid receptor expressed in HEK 293 cells; in-house prep) in a final volume of 200 μl binding buffer (5% DMSO, 50 mM Trizma base, pH 7.4). Non-specific binding was determined in the presence of 10 μM unlabeled naloxone or U69,593. All reactions were performed in 96-well polypropylene plates for 1 hr at a temperature of about 25° C. Binding reactions were determined by rapid filtration onto 96-well Unifilter GF/C filter plates (Packard) presoaked in 0.5% polyethylenimine (Sigma). Harvesting was performed using a 96-well tissue harvester (Packard) followed by five filtration washes with 200 μl ice-cold binding buffer. Filter plates were subsequently dried at 50° C. for 1-2 hours. Fifty μl/well scintillation cocktail (MicroScint20, Packard) was added and plates were counted in a Packard Top-Count for 1 min/well.

κ-opioid Receptor Binding Data:

Typically, the Compounds of the Invention will have a Ki (nM) of about 10,000 or less for κ receptors. In certain embodiments, Compounds of the Invention will have a Ki (nM) of about 5000 or less; or about 1000 or less; or about 500 or less; or about 450 or less; or about 350 or less; or about 200 or less; or about 100 or less; or about 50 or less; or about 10 or less.

κ-Opioid Receptor Functional Assay Procedures:

Functional [$^{35}$S]GTPγS binding assays were conducted as follows. Kappa opioid receptor membrane solution was prepared by sequentially adding final concentrations of 0.026 μg/μl kappa membrane protein (in-house), 10 μg/mL saponin, 3 μM GDP and 0.20 nM [$^{35}$S]GTPγS to binding buffer (100 mM NaCl, 10 mM MgCl$_2$, 20 mM HEPES, pH 7.4) on ice. The prepared membrane solution (190 μl/well) was transferred to 96-shallow well polypropylene plates containing 10 μl of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 μl ice-cold binding buffer (10 mM NaH$_2$PO$_4$, 10 mM Na$_2$HPO$_4$, pH 7.4). Filter plates were subsequently dried at 50° C. for 2-3 hours. Fifty μl/well scintillation cocktail (MicroScint20, Packard) was added and plates were counted in a Packard Top-Count for 1 min/well.

κ-Opioid Receptor Functional Data:

κ GTP EC$_{50}$ is the concentration of a compound providing 50% of the maximal response for the compound at a κ receptor. Compounds of the Invention typically will have a κ GTP EC$_{50}$ (nM) of about 10,000 or less to stimulate κ opioid receptor function. In certain embodiments, Compounds of the Invention will have a κ GTP EC$_{50}$ (nM) of about 5000 or less; or about 2000 or less; or about 1500 or less; or about 1000 or less; or about 600 or less; or about 100 or less; or about 50 or less; or about 25 or less; or about 10 or less.

κ GTP Emax (%) is the maximal effect elicited by a compound relative to the effect elicited by U69,593. Typically, Compounds of the Invention will have a κ GTP Emax (%) of greater than about 50%. In certain embodiments, Compounds of the Invention will have a κ GTP Emax (%) of greater than about 75%; or greater than about 90%; or greater than about 100%.

δ-opioid Receptor Binding Assay Procedures:

δ-opioid Receptor Binding Assay Procedures can be conducted as follows. Radioligand dose-displacement assays use 0.2 nM [$^3$H]-Naltrindole (NEN; 33.0 Ci/mmole) with 10-20 µg membrane protein (recombinant delta opioid receptor expressend in CHO-K1 cells; Perkin Elmer) in a final volume of 500 µl binding buffer (5 mM MgCl$_2$, 5% DMSO, 50 mM Trizma base, pH 7.4). Non-specific binding is determined in the presence of 25 µm M unlabeled naloxone. All reactions are performed in 96-deep well polypropylene plates for 1 hr at a temperature of about 25° C. Binding reactions are determined by rapid filtration onto 96-well Unifilter GF/C filter plates (Packard) presoaked in 0.5% polyethylenimine (Sigma). Harvesting is performed using a 96-well tissue harvester (Packard) followed by five filtration washes with 500 µl ice-cold binding buffer. Filter plates are subsequently dried at 50° C. for 1-2 hours. Fifty µl/well scintillation cocktail (MicroScint20, Packard) is added and plates are counted in a Packard Top-Count for 1 min/well.

δ-opioid Receptor Binding Data:

Compounds of the Invention will have a Ki (nM) for δ receptors of about 10 or more; or about 100 or more; or about 250 or more; or about 350 or more; or about 500 or more; or about 1000 or more; or about 2500 or more; or about 3000 or more; or about 4000 or more; or even about 10,000 or more.

δ-Opioid Receptor Functional Assay Procedures:

Functional [$^{35}$S]GTPγS binding assays can be conducted as follows. Delta opioid receptor membrane solution is prepared by sequentially adding final concentrations of 0.026 µg/µl delta membrane protein (Perkin Elmer), 10 µg/mL saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µl/well) is transferred to 96-shallow well polypropylene plates containing 10 µl of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Packard) using a 96-well tissue harvester (Packard) and followed by three filtration washes with 200 µl ice-cold binding buffer (10 mM NaH$_2$PO$_4$, 10 mM Na$_2$HPO$_4$, pH 7.4). Filter plates are subsequently dried at 50° C. for 1-2 hours. Fifty µl/well scintillation cocktail (MicroScint20, Packard) is added and plates are counted in a Packard Top-count for 1 min/well.

δ-Opioid Receptor Functional Data:

δ GTP EC$_{50}$ is the concentration of a compound providing 50% of the maximal response for the compound at a δ receptor. Compounds of the Invention typically have a δ GTP EC$_{50}$ (nM) of about 10,000 or more to stimulate δ opioid receptor function. In certain embodiments, Compounds of the Invention will have a δ GTP EC$_{50}$ (nM) of about 1000 or more; or about 100 or more; or about 90 or more; or about 50 or more; or about 25 or more; or about 10 or more.

δ GTP Emax (%) is the maximal effect elicited by a compound relative to the effect elicited by met-enkephalin. Typically, Compounds of the Invention will have a δ GTP Emax (%) of less than about 1%. In certain embodiments, Compounds of the Invention will have a δ GTP Emax (%) of less than about 5%; or less than about 10%; or less than about 20%; or less than about 50%; or less than about 75%; or less than about 90%; or less than about 100%; or less than about 110%.

In particular embodiments, Compounds of the Invention have a mu Ki (nM) of less than 1000; a mu GTP EC$_{50}$ (nM) of less than 1000; a mu GTP Emax (%) of less than 50; a kappa Ki (nM) of less than 1000; a kappa GTP EC$_{50}$ (nM) of less than 1000; and a kappa GTP Emax (%) of greater than 50.

In other embodiments, certain Compounds of the Invention have a mu Ki (nM) of less than 500; a mu GTP EC$_{50}$ (nM) of less than 500; a mu GTP Emax (%) of less than 20; a kappa Ki (nM) of less than 1000; a kappa GTP EC$_{50}$ (nM) of less than 500; and a kappa GTP Emax (%) of greater than 30%.

In other embodiments, certain Compounds of the Invention have a mu Ki (nM) of less than 100; a mu GTP EC$_{50}$ (nM) of less than 100; a mu GTP Emax (%) of less than 10%; a kappa Ki (nM) of less than 100; a kappa GTP EC$_{50}$ (nM) of less than 100; and a kappa GTP Emax (%) of greater than 95%.

Assays to Assess Oral Absorption

Oral absorption can be measured using standard techniques for assessing pharmacokinetic parameters known in the art. For example, a Compound of the Invention is orally administered at a known concentration to a laboratory animal such as a rat. At various time points after oral administration, blood samples are drawn, and the amount of the compound in the plasma is measured, using for example HPLC analysis with UV detection.

In Vivo Assays for Assessment of Gastric Motility

The rat gastric motility assay (Green (1959) *Br. J. Pharmacol.* 14: 26-34) can be used to assess the constipation relieving action of a Compound of the Invention in a model of GI transit. For the GI transit assay, rats are fasted for 18-22 hr. A test compound can be administered orally in 0.5% methylcellulose in a volume of 10 mL/kg. One hour after compound administration, rats are given a 7.5% suspension of charcoal meal in 0.5% methylcellulose orally in a volume of 0.5 mL/100 g body weight. One half hour following the charcoal meal, the rats are sacrificed in a rising concentration of CO$_2$, and the small intestine is excised from the pylorus to the ileocecal valve. The length of the small intestine and the total distance traveled by the charcoal meal then are measured in centimeters. The percent transit is calculated as follows:

% Transit=[(total distance traveled)/(length of the small intestine)]×100.

Statistical Analysis

Data analysis can be performed on the % transit data by ANOVA, and followed by post hoc analysis with Fisher's PLSD. The level of significance is set at P<0.05.

Pharmaceutical Compositions

Although a Compound of the Invention can be administered to a mammal in the form of a raw chemical without any other components present, the compound is preferably administered as part of a pharmaceutical composition containing an effective amount of the compound combined with a suitable pharmaceutically acceptable carrier. Such a carrier can be selected from pharmaceutically acceptable excipients and auxiliaries based on the route of administration.

As used herein, "an effective amount" of a Compound of the Invention refers to an amount effective for: (a) treating or preventing constipation, particularly mu opioid agonist induced constipation; (b) detectably inhibiting mu opioid receptor function in a cell; or (c) detectably activating kappa opioid receptor function in a cell.

Pharmaceutical compositions within the scope of the present invention include all compositions where a Compound of the Invention is combined with a pharmaceutically acceptable carrier. In a preferred embodiment, the compound is present in the composition in an amount effective to achieve its intended therapeutic purpose. While individual needs may vary, a determination of optimal ranges of effective amounts of each compound is within the skill of the art. Typically, the Compound of the Invention is administered to a mammal, e.g. a human, orally at a dose of from about 0.0025 to about 1500 mg per kg body weight of the mammal, or an equivalent amount of a pharmaceutically acceptable salt, prodrug or solvate thereof, per day to treat or prevent constipation, particularly mu opioid receptor-induced constipation. A useful oral dose of a compound of the present invention administered to a mammal is from about 0.025 to about 50 mg per kg body weight of the mammal, or an equivalent amount of the pharmaceutically acceptable salt, prodrug or solvate thereof. A unit oral dose may comprise from about 0.01 to about 50 mg, and preferably about 0.1 to about 10 mg, of a compound. The unit dose can be administered one or more times daily, e.g. as one or more tablets or capsules, each containing from about 0.01 mg to about 50 mg of the compound, or an equivalent amount of a pharmaceutically acceptable salt, prodrug or solvate thereof.

A pharmaceutical composition of the present invention can be administered to any animal that may experience the beneficial effects of a compound of the present invention. Foremost among such animals are mammals, e.g., humans and companion animals, although the invention is not intended to be so limited.

A pharmaceutical composition of the present invention can be administered by any means that achieves its intended purpose. For example, administration can be by the oral or rectal route. The dosage administered and the route of administration will vary depending upon the circumstances of the particular subject, and taking into account such factors as age, gender, health, and weight of the recipient, condition or disorder to be treated, type of concurrent treatment (if any), the frequency of treatment, and the nature and extent of the desired effect.

In one embodiment, a pharmaceutical composition of the present invention can be administered orally and is formulated into tablets, dragees, capsules or an oral liquid preparation. In one embodiment, the oral formulation comprises extruded multiparticulates comprising the compound of the invention.

In another embodiment, a pharmaceutical composition of the present invention is formulated to be administered rectally, i.e., as suppositories.

A pharmaceutical composition of the present invention can contain from about 0.01 to 99 percent by weight, and preferably from about 0.25 to 75 percent by weight, of active compound(s).

A pharmaceutical composition of the present invention is preferably manufactured in a manner which itself will be known in view of the instant disclosure, for example, by means of conventional mixing, granulating, dragee-making, dissolving, extrusion, or lyophilizing processes. Thus, pharmaceutical compositions for oral use can be obtained by combining the active compound with solid excipients, optionally grinding the resulting mixture and processing the mixture of granules, after adding suitable auxiliaries, if desired or necessary, to obtain tablets or dragee cores. Alternatively, the pharmaceutical composition can be prepared as extruded multiparticulates.

Suitable excipients include fillers such as saccharides (for example, lactose, sucrose, mannitol or sorbitol), cellulose preparations, calcium phosphates (for example, tricalcium phosphate or calcium hydrogen phosphate), as well as binders such as starch paste (using, for example, maize starch, wheat starch, rice starch, or potato starch), gelatin, tragacanth, methyl cellulose, hydroxypropylmethylcellulose, sodium carboxymethylcellulose, and/or polyvinyl pyrrolidone. If desired, one or more disintegrating agents can be added, such as the above-mentioned starches and also carboxymethyl-starch, cross-linked polyvinyl pyrrolidone, agar, or alginic acid or a salt thereof, such as sodium alginate.

Auxiliaries can be included, and they are typically flow-regulating agents and lubricants such as, for example, silica, talc, stearic acid or salts thereof (e.g., magnesium stearate or calcium stearate), and polyethylene glycol. Dragee cores can be provided with suitable coatings that are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate can be used. Dye stuffs or pigments may be added to the tablets or dragee coatings, for example, for identification or in order to characterize combinations of active compound doses.

Examples of other pharmaceutical preparations that can be used orally include push-fit capsules made of gelatin, or soft, sealed capsules made of gelatin and a plasticizer such as glycerol or sorbitol. The push-fit capsules can contain a compound in the form of granules, which may be mixed with fillers such as lactose, binders such as starches, and/or lubricants such as talc or magnesium stearate and, optionally, stabilizers, or in the form of extruded multiparticulates. In soft capsules, the active compounds are preferably dissolved or suspended in suitable liquids, such as fatty oils or liquid paraffin. In addition, stabilizers may be added.

Possible pharmaceutical preparations for rectal administration include, for example, suppositories, which typically consist of a combination of one or more active compounds with a suppository base. Suitable suppository bases include natural and synthetic triglycerides, and paraffin hydrocarbons, among others. It is also possible to use gelatin rectal capsules consisting of a combination of active compound with a base material such as, for example, a liquid triglyceride, polyethylene glycol, or paraffin hydrocarbon.

In one embodiment, pharmaceutical compositions of the invention are prepared by incorporating Compounds of the Invention into a controlled release formulation. Controlled release formulations are useful for a variety of purposes, including situations where a steady state plasma level of a Compound of the Invention is to be maintained. One manner in which these steady state plasma levels can be obtained is by using appropriate technologies, e.g., controlled-release formulations, selected to provide an appropriate release profile. The appropriate release profile can be achieved, for example, using single or multiparticulate delivery systems. Examples of single delivery systems include, but are not limited to, wax matrix tablets, hydrophilic matrix tablets and tablets with controlled-release coatings. Examples of multiparticulate systems include, but are not limited to, matrix systems such as melt extruded multiparticulates (MEMs), or systems based on controlled release coatings such as coated-beads.

In one embodiment, a pharmaceutical composition of the present invention provides a therapeutic steady state plasma level of a Compound of the Invention for a duration of from about 12 hr to about 24 hr following oral administration. In another embodiment, a pharmaceutical composition of the present invention provide a therapeutic steady state plasma level of a Compound of the Invention for a duration of from about 6 h to about 12 following oral administration.

The method of the present invention, i.e., a method for treating or preventing constipation, can further comprise administering a second therapeutic agent to the patient in combination with a Compound of the Invention (which would therefore be a first therapeutic agent). In one embodiment, the second therapeutic agent is administered in an effective amount.

Effective amounts of the second therapeutic agents will generally be known to those skilled in the art depending on the identity of the second therapeutic agent. However, it is within the skilled artisan's purview to determine the optimal effective-amount range of the second therapeutic agent.

A Compound of the Invention (i.e., the first therapeutic agent) and second therapeutic agent can act additively or synergistically to treat the same condition. Alternatively, the first and second therapeutic agents can be used to treat different conditions, and may show no additive or synergistic action. In one embodiment, a Compound of the Invention is administered to the patient concurrently with the second therapeutic agent; for example, in a single composition comprising an effective amount of a Compound of the Invention and a second therapeutic agent. Accordingly, the present invention further provides a pharmaceutical composition comprising a combination of an effective amount of a Compound of the Invention, an effective amount of a second therapeutic agent, and a pharmaceutically acceptable carrier. Alternatively, a Compound of the Invention and the second therapeutic agent can be concurrently administered in separate compositions. In another embodiment, a Compound of the Invention is administered prior or subsequent to administration of the second therapeutic agent. In this embodiment, the Compound of the Invention is preferably administered while the second therapeutic agent exerts its therapeutic effect, or the second therapeutic agent is administered while the Compound of the Invention exerts its therapeutic effect.

The second therapeutic agent is preferably a mu opioid agonist, since the primary benefit of the present invention is to treat or prevent constipation otherwise caused by mu agonist analgesic therapy. Examples of useful mu opioid agonists include, but are not limited to, alfentanil, allylprodine, alphaprodine, benzylmorphine, codeine, desomorphine, dextromoramide, diamorphone, dihydrocodeine, dihydromorphine, ethylmorphine, etorphin, fentanyl, heroin, hydrocodone, hydromorphone, isomethadone, ketobemidone, levorphanol, lofentanil, meperidine, methadone, morphine, nicomorphine, normethadone, normorphine, opium, oxycodone, oxymorphone, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Alternatively, the second therapeutic agent can be a non-opioid analgesic such as, e.g., a non-steroidal anti-inflammatory agent (NSAID), an anti-migraine agent, an anti-emetic agent, a Cox-II inhibitor, a lipoxygenase inhibitor, a β-adrenergic blocker, an anti-convulsant, an anti-depressant, an anti-cancer agent, an agent for treating addictive disorder, an agent for treating Parkinson's disease and parkinsonism, an agent for treating anxiety, an agent for treating epilepsy, an agent for treating a seizure, an agent for treating stroke, an agent for treating a pruritic condition, an agent for treating psychosis, an agent for treating ALS, an agent for treating a cognitive disorder, an agent for treating dyskinesia, or a mixture thereof.

Examples of useful NSAIDs include aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof.

Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone.

For a more detailed description of the NSAIDs, see Paul A. Insel, Analgesic Antipyretic and Antiinflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996) and Glen R. Hanson, Analgesic, Antipyretic and Anti Inflammatory Drugs in Remington: The Science and Practice of Pharmacy Vol II 1196 1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

EXAMPLES

The following examples are illustrative and not limiting of the compounds, compositions and methods of the present invention. Suitable modifications and adaptations of the variety of conditions and parameters normally encountered in clinical therapy and which are obvious to those skilled in the art in view of this disclosure are within the spirit and scope of the invention.

Example 1

3-cyclopropylmethyl-9-hydroxy-3,6,11-trimethyl-1,2,3,4,5,6-hexahydro-2,6-methano-benzo[d]azocinium (1)

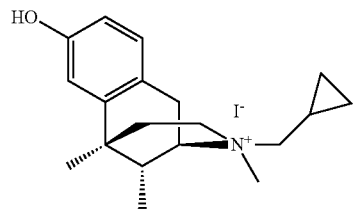

Compound (1) was prepared according to the following protocol.

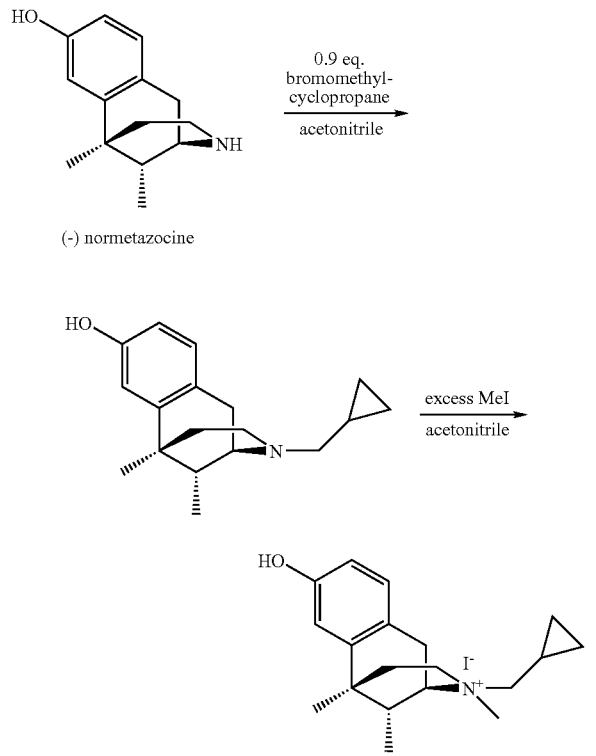

(-) normetazocine 150 mgs (−)-normetazocine (0.691 mmol, mw=217, Sigma) were suspended in 1.5 mls dry acetonitrile and stirred with a magnetic stir bar in a 50-ml vial with a screw-top septum under nitrogen. 0.622 mmol bromomethylcyclopropane (mw=135, density=1.392) were added dropwise with a syringe. The mixture was stirred for 20 hours. When the reaction was complete (as monitored by LC/MS and TLC), the solvent was removed. Impurities were removed by flash chromatography using a column of alumina basic as the stationary media with a gradient of EtOAc in hexane followed by 15% MeOH in DCM as the eluent. The purified material was concentrated in vacuo. The product was suspended in 1.5 mls dry acetonitrile, and an excess of methyl iodide (0.5 ml) was added in one portion. The solution was stirred at ambient temperature for three hours and the reaction followed by LC/MS and TLC. The volatile materials were removed in vacuo. The resulting title compound was pure, with 104 mgs of 100% pure product collected as a yellow solid.

The identity of compound (1) was verified by LC/MS and $^1$HNMR.

MS: 286

$^1$HNMR (CD$_3$OD): δ (ppm) 7.06-7.02 (bd, 1H, J=8.33), 6.78-6.76 (bd, 1H, J-2.41), 6.71-6.67 (m, 1H), 3.85-3.71 (m, 2H), 3.40-3.34 (m, 3H), 3.27-3.16 (m, 3H), 3.08-2.84 (m, 2H), 2.55-2.23 (m, 2H), 1.55-1.45 (m, 4H), 1.25-1.18 (m, 1H), 1.02-0.97 (m, 3H), 0.90-0.79 (m, 2H), 0.62-0.44 (m, 2H).

Example 2

3-allyl-9-hydroxy-3,6,11-trimethyl-1,2,3,4,5,6-hexahydro-2,6-methano-benzo[d]azocinium (2)

Compound (2) was prepared according to the following protocol.

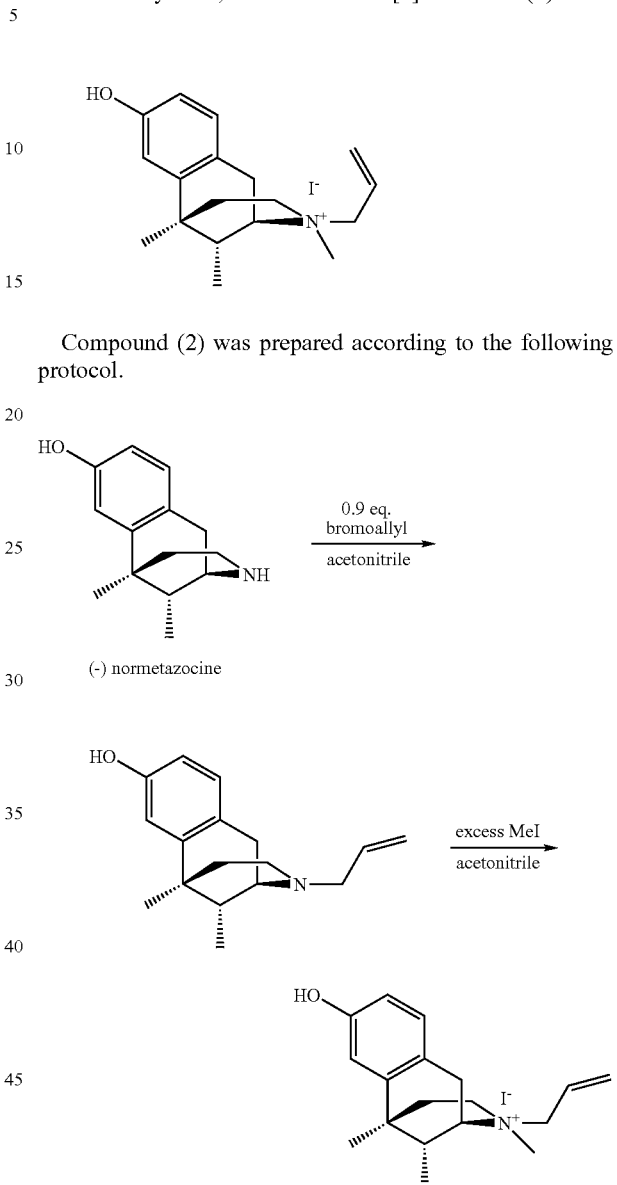

(-) normetazocine 150 mgs (−)-normetazocine (0.691 mmol, mw=217, Sigma) were suspended in 1.5 mls dry acetonitrile and stirred with a magnetic stir bar in a 50-ml vial with a screw-top septum under nitrogen. 0.622 mmol bromoallyl (mw=121, density=1.398) were added dropwise with a syringe. The mixture was stirred for 20 h. When the reaction was complete, (as monitored by LC/MS and TLC), the solvent was removed. Impurities were removed by flash chromatography using a column of alumina basic as the stationary media with a gradient of EtOAc in hexane followed by 15% MeOH in DCM as the eluent. Then, purification was continued by chromatography using a column of normal silica with the same two solvent systems as above. The purified material was concentrated in vacuo. The purpose of the two different media is to clean up the residue of the di-substituted side product and remaining starting material. The product was suspended in dry acetonitrile and an excess of methyl iodide (0.5 ml) was added in one portion. The solution was stirred at ambient temperature for three hours, and the reaction was followed by LC/MS and TLC. The volatile materials were removed in vacuo. The resulting title compound was pure, with 84 mgs of 100% pure product collected as a yellow solid.

The identity of compound (2) was verified by LC/MS and $^1$HNMR.

MS: 272

$^1$HNMR (CD$_3$OD): δ (ppm) 7.08-7.04 (bd, 1H, J=8.11), 6.79-6.76 (bd, 1H, J-2.41), 6.72-6.68 (m, 1H), 6.20-6.07 (m, 1H), 5.83-5.72 (m, 2H), 4.32-4.24 (1, 1H, J=13.81, J=7.24), 4.00-3.92 (m, 1H), 3.62-3.58 (m, 1H), 3.42-3.34 (m, 1H), 3.28-3.15 (m, 5H), 3.02-2.93 (m, 1H), 2.52-2.44 (m, 1H), 2.33-2.22 (m, 1H), 1.58-1.44 (m, 4H), 0.99-0.95 (m, 3H).

Example 3

The following Tables provide results on the efficacy of binding and activity response of exemplified Compounds of the Invention at the μ-, δ- and κ-opioid receptors.

In TABLE 1, binding efficacy of certain Compounds of the Invention to the μ-, δ- and κ-opioid receptors was determined as described above.

In TABLE 2, activity response of certain Compounds of the Invention to the μ-, δ- and κ-opioid receptors was determined as described above for functional assays.

TABLE 1

Binding Efficacy of Benzomorphan Compounds

| Ref. No. | Compound | Ki [mean ± SEM] (nM) | | |
|---|---|---|---|---|
| | | μ | δ | κ |
| 1 | [structure] | 23.03 ± 6.64 | | 4.33 ± 1.21 |
| 2 | [structure] | 56.45 ± 9.11 | | 10.3 ± 3.03 |

TABLE 2

Activity Response of Benzomorphan Compounds

| Ref. No. | Compound | GTPγS (EC$_{50}$: nM, E$_{max}$: %) [mean ± SEM] | | | | | |
|---|---|---|---|---|---|---|---|
| | | μ | | δ | | κ | |
| | | EC$_{50}$ | E$_{max}$ | EC$_{50}$ | E$_{max}$ | EC$_{50}$ | E$_{max}$ |
| 1 | [structure] | >20 μM | 16 ± 14.64 | | | 77.28 ± 14.74 | 50 ± 7.51 |
| 2 | [structure] | >20 μM | 3.67 ± 1.33 | | | 268.26 ± 46.44 | 27.33 ± 3.38 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference in their entirety.

What is claimed is:

1. A compound of Formula I:

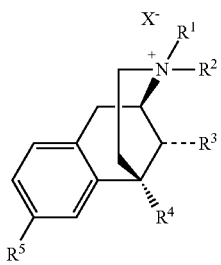

I wherein $R^1$ and $R^2$ are each independently selected from the group consisting of —$(C_1-C_{10})$alkyl, —$(C_2-C_{10})$alkenyl, —$(C_2-C_{10})$alkynyl, —$(C_3-C_{12})$cycloalkyl, —$(C_3-C_{12})$cycloalkenyl, —$(CH_2)_n$—O—$(CH_2)_n$—$CH_3$, $(C_1-C_{10})$ alkoxy, C(halo)$_3$, —CH(halo)$_2$, —CH$_2$(halo), C(O)R$^6$, —C(O)O—$(C_1-C_{10})$alkyl, and —$(CH_2)_n$—N(R$^7$)$_2$, each of which is optionally substituted by 1, 2, or 3 independently selected $R^8$ groups;

wherein if $R^1$ and $R^2$ are both —$(C_1-C_{10})$alkyl, at least one of $R^1$ and $R^2$ is substituted by at least one $R^8$ group that is other than —$(C_1-C_{10})$alkyl;

$R^3$ and $R^4$ are each independently selected from (a) —H; or (b) —$(C_1-C_5)$alkyl, —$(C_2-C_5)$alkenyl, and —$(C_2-C_5)$alkynyl;

$R^5$ is selected from (a) —H, halo, —C(halo)$_3$, —CH(halo)$_2$, and —CH$_2$(halo)

(b) —$(C_1-C_5)$alkyl, —$(C_2-C_5)$alkenyl, —$(C_2-C_5)$alkynyl, —$(CH_2)_n$—O—$(CH_2)_n$—$CH_3$, —$(C_1-C_5)$ alkoxy, each of which is optionally substituted with 1, 2, or 3 independently selected $R^8$ groups;

$R^6$ is selected from —H, —$(C_1-C_{10})$alkyl, —$(C_2-C_{10})$alkenyl, —$(C_2-C_{10})$alkynyl, and —$(C_1-C_{10})$alkoxy;

each $R^7$ is independently selected from —H, —$(C_1-C_{10})$alkyl, —$(C_2-C_{10})$alkenyl, and —$(C_2-C_{10})$alkynyl;

each $R^8$ is independently selected from —OH, halo, —$(C_1-C_{10})$alkyl, —$(C_2-C_{10})$alkenyl, —$(C_2-C_{10})$alkynyl, —$(C_1-C_{10})$alkoxy, —$(C_3-C_{12})$cycloalkyl, —CHO, —C(O)OH, —C(halo)$_3$, —CH(halo)$_2$, —CH$_2$(halo), and —$(CH_2)_n$—O—$(CH_2)_n$—$CH_3$;

X$^-$ is an organic or inorganic anion, selected from the group consisting of sulfate; citrate; acetate; dichloroacetate; trifluoroacetate; oxalate; halide, such as chloride, bromide, iodide; nitrate; bisulfate; phosphate; acid phosphate; isonicotinate; lactate; salicylate; acid citrate; tartrate; oleate; tannate; pantothenate; bitartrate; ascorbate; succinate; maleate; gentisinate; fumarate; gluconate; glucoronate; saccharate; formate; mandelate; formate; arginate; carboxylate; benzoate; glutamate; methanesulfonate; ethanesulfonate; benzenesulfonate; p-toluenesulfonate; and pamoate (i.e., 1,1'-methylene-bis-(2-hydroxy-3-naphthoate));

each n is independently selected from an integer from 0, 1, 2, 3, 4, 5, or 6 or a pharmaceutically acceptable salt thereof.

2. A compound of claim 1, wherein the compound is a pharmaceutically acceptable salt of a compound of Formula I.

3. A compound of claim 1, wherein at least one of $R^1$ and $R^2$ is a —$(C_1-C_{10})$ alkyl, each of which is substituted by one $R^8$ group, wherein the $R^8$ group is independently selected from —$(C_3-C_{12})$cycloalkyl.

4. A compound of claim 3, wherein each $R^8$ is independently selected from cyclopropyl, cyclopentyl, cyclohexyl, cycloheptyl, cyclooctyl, cyclononyl and cyclodecyl.

5. A compound of claim 1, wherein at least one of $R^1$ and $R^2$ are selected from —$CH_2$-cyclopropyl, —$CH_2CH_2$-cyclopropyl, and —$CH_2CH_2CH_2$-cyclopropyl.

6. A compound of claim 1, wherein at least one of $R^1$ and $R^2$ is a —$(C_2-C_{10})$alkenyl.

7. A compound of claim 1, wherein at least one of $R^1$ and $R^2$ is —$CH_2CH=CH_2$.

8. A compound of claim 1, wherein $R^1$ is —$CH_3$ and $R^2$ is —$CH_2$-cyclopropyl or —$CH_2$—CH=$CH_2$.

9. A compound of claim 1, wherein $R^3$ and $R^4$ are each independently selected from —$(C_1-C_5)$alkyl.

10. A compound of claim 1, wherein $R^5$ is —$(CH_2)_n$—O—$(CH_2)_n$—$CH_3$.

11. A compound of claim 1, wherein each n is independently selected from 1, 2 and 3.

12. A pharmaceutical composition comprising an effective amount of a compound of claim 1, and a pharmaceutically acceptable carrier or excipient.

13. A kit comprising a container containing an effective amount of a compound of claim 1.

14. A method for preparing a composition, comprising the step of admixing a compound or pharmaceutically acceptable salt of claim 1 and a pharmaceutically acceptable carrier or excipient.

* * * * *